(12) United States Patent
Böcking et al.

(10) Patent No.: US 8,114,625 B2
(45) Date of Patent: Feb. 14, 2012

(54) METHOD FOR CELL ANALYSIS

(75) Inventors: Alfred Böcking, Aachen (DE); Dietrich Meyer-Ebrecht, Aachen (DE)

(73) Assignee: Motic China Group Co. Ltd., Xiamen (CN)

( * ) Notice: Subject to any disclaimer, the term of this patent is extended or adjusted under 35 U.S.C. 154(b) by 781 days.

(21) Appl. No.: 11/839,141

(22) Filed: Aug. 15, 2007

(65) Prior Publication Data

US 2008/0044849 A1 Feb. 21, 2008

Related U.S. Application Data

(60) Provisional application No. 60/845,861, filed on Sep. 20, 2006.

(30) Foreign Application Priority Data

Aug. 15, 2006 (DE) .......................... 10 2006 038 335

(51) Int. Cl.
*G01N 1/30* (2006.01)
*G01N 33/48* (2006.01)
*G01N 33/483* (2006.01)
*C12Q 1/68* (2006.01)
*C12Q 1/02* (2006.01)

(52) U.S. Cl. ........................... 435/40.5; 435/6.1; 435/29

(58) Field of Classification Search ........................ None
See application file for complete search history.

(56) References Cited

U.S. PATENT DOCUMENTS

| 4,513,438 | A | * | 4/1985 | Graham et al. ............... 382/134 |
| 5,281,517 | A | | 1/1994 | Bacus et al. |
| 6,007,996 | A | | 12/1999 | McNamara et al. |
| 6,100,051 | A | * | 8/2000 | Goldstein et al. ............ 435/40.5 |
| 6,546,123 | B1 | | 4/2003 | McLaren et al. |

FOREIGN PATENT DOCUMENTS

| DE | 10128552 | | 12/2002 |
| DE | 10128552 | A1 | 12/2002 |
| EP | 1065496 | | 1/2001 |
| EP | 1811281 | | 7/2007 |

OTHER PUBLICATIONS

Natalia Pomjanski, et al.; "Early Diagnosis of Mesothelioma in Serous Effusions Using AgNOR Analysis;" from the Apr. 2001 issue of the Journal of Analytical and Quantitative Cytology and Histology.

* cited by examiner

*Primary Examiner* — Vera Afremova
(74) *Attorney, Agent, or Firm* — Clark Hill PLC

(57) ABSTRACT

The invention describes a method for cell analysis in which the cells to be analyzed are adhesively applied to a slide and stained with a first stain. A first digital image is then taken and stored of the cells applied to the slide and stained. After the first digital image is taken, these same cells are treated with a second stain while on the same slide in such a way that their optically measurable properties change. A second digital image is then taken of the cells applied to the slide and stored. According to the invention, a group of preparations with cells to be analyzed is first stained with a stain of a highly sensitive analysis method, and only the preparations with positive findings are further processed.

23 Claims, 6 Drawing Sheets

| Analytical Step\Diagnosis | Step 1 Morphology | Step 2 IC-Marker | Step 3 DNA-ICM | Step 4 AgNOR |
|---|---|---|---|---|
| Reactive Mesothelioma | Unremarkable | Calretinin+ BerEP4- | Euploid | <4.5 |
| Malignant Mesothelioma | Remarkable | Calretinin+ BerEP4- | Polyploid | >4.5 |
| Metastasizing Cancer | Remarkable | Calretinin- BerEP4+ | Aneuploid | >4.5 |

FIG. 6

METHOD FOR CELL ANALYSIS

CROSS-REFERENCE TO RELATED APPLICATION:

This application claims priority from U.S. Provisional Patent Application No. 60/845,861, filed Sep. 20, 2006, and from German Patent Application DE 10 2006 038 335.4, filed Aug. 15, 2006, the disclosure of both of which is incorporated herein.

BACKGROUND OF THE INVENTION

The invention relates to the field of cell analysis, and in particular to a method of cell analysis in which the cells to be analyzed are adhesively applied to a slide and stained with a first stain, where a first digital picture is taken of the stained cells applied to the slide and then stored, where the same cells on the slide are treated with a second stain after the first digital picture is taken so that their optically measurable characteristics change, and where a second digital picture is then taken of the same cells applied to the slide and then stored.

German Patent No. DE 101 28 552 discloses an analytical method of this type and a device for performing this type of analysis. This publication describes methods and devices in which the cells to be analyzed are adhesively applied to a slide and subjected to various treatments for the purpose of ascertaining certain properties of the cells.

These treatments include in particular the "staining" of the cells, where the cells are brought into contact with a chemical substance that triggers various chemical reactions in the cells according to the properties thereof, where the chemical reactions usually precipitate in a change in optically perceivable cell properties and change the transmission, absorption and/or luminescence behavior of the cells. In the simplest case, the cells change color based on their properties allowing the cells to be separated into different categories such as normal/abnormal based on their color or the patterns of their spatial distribution of color.

In the present application, it is hereby stressed that although this application exclusively speaks of "staining" by means of a "stain", these terms are hereinafter to be understood as all forms of treatment of the cells adhesively applied to a slide that change the emission, transmission, and/or absorption behavior of the cells in relation to electromagnetic waves, in particular in relation to electromagnetic waves with wavelengths in the visible range. "Staining" in this sense can thus also mean that the cells are exposed not to a chemical, yet rather to a physical treatment such as, for example, irradiation or heat treatment. The method described herein is especially advantageous since it describes an analysis of bodily cells that facilitates the early diagnosis of cancer with a high degree of accuracy.

It is advantageous for multiple reasons to base the diagnosis of cancer, in particular for the purpose of preventive cancer care, on the analysis of cell samples instead of tissue samples (histology, although the prevalent routine diagnostic tool today, involves interventions resulting in a loss of blood) or organ imaging (x-rays, ultrasound, etc.). The cells are the earliest manifestation of a developing cancer. The earlier the intervention is performed, the greater the chances of the disease being cured. Furthermore, cell samples are gathered by means of brush smear or fine needle biopsy and involve no loss of blood and little or no pain. Patients are therefore more readily accepting of examinations, and the examination costs are kept low.

A high degree of accuracy is required particularly in preventive care diagnostic applications. The rate of false negatives must remain low (high sensitivity) so that positive findings are not overlooked and samples are not looked upon with a false sense of security. However, the false positive rate must also remain low (high specificity), since the portion of negative cases will heavily prevail in the preventive care phase and each false positive finding leads to costly follow-up examinations or absolutely unnecessary therapy not to mention legal consequences. None of the routinely employed cytopathological diagnostic methods offers high sensitivity and specificity at the same time. Furthermore, cytopathological analyses are usually time-consuming, demand highly trained personnel and are thus costly.

The method described in DE 101 28 552 A1 has many advantages. The accuracy of the diagnosis is increased to the required degree through the fusion of cell-specific properties that are gathered in a series of analytical steps. This is achieved by having the complementary analyses performed on the same microscopic preparation by means of interposed destaining and restaining and by having the analysis values assigned to individual cells.

Nevertheless, a need exists for a method of cell analysis with high sensitivity and high specificity. The present invention meets this need.

BRIEF SUMMARY OF THE INVENTION

The present invention is a microscopic analysis method for cytological preparations in which a stained cell preparation is removed following analysis and is then analyzed from a different angle after being stained once again. In this process, the individual cells must be precisely aligned following each restaining process. The analysis results therefore not only apply across the board for the preparation, but can be individually assigned to the analyzed cells and merged into a multi-dimensional cell-specific characteristic vector.

BRIEF DESCRIPTION OF THE SEVERAL VIEWS OF THE DRAWINGS

The organization and manner of the structure and operation of the invention, together with further objects and advantages thereof, may best be understood by reference to the following description, taken in connection with the accompanying non-scale drawings, wherein like reference numerals identify like elements in which:

FIG. 6 is a table of the diagnostic significance of the results of the methods of the embodiments of the invention.

DETAILED DESCRIPTION OF THE PREFERRED EMBODIMENTS OF THE INVENTION

Figure 1:
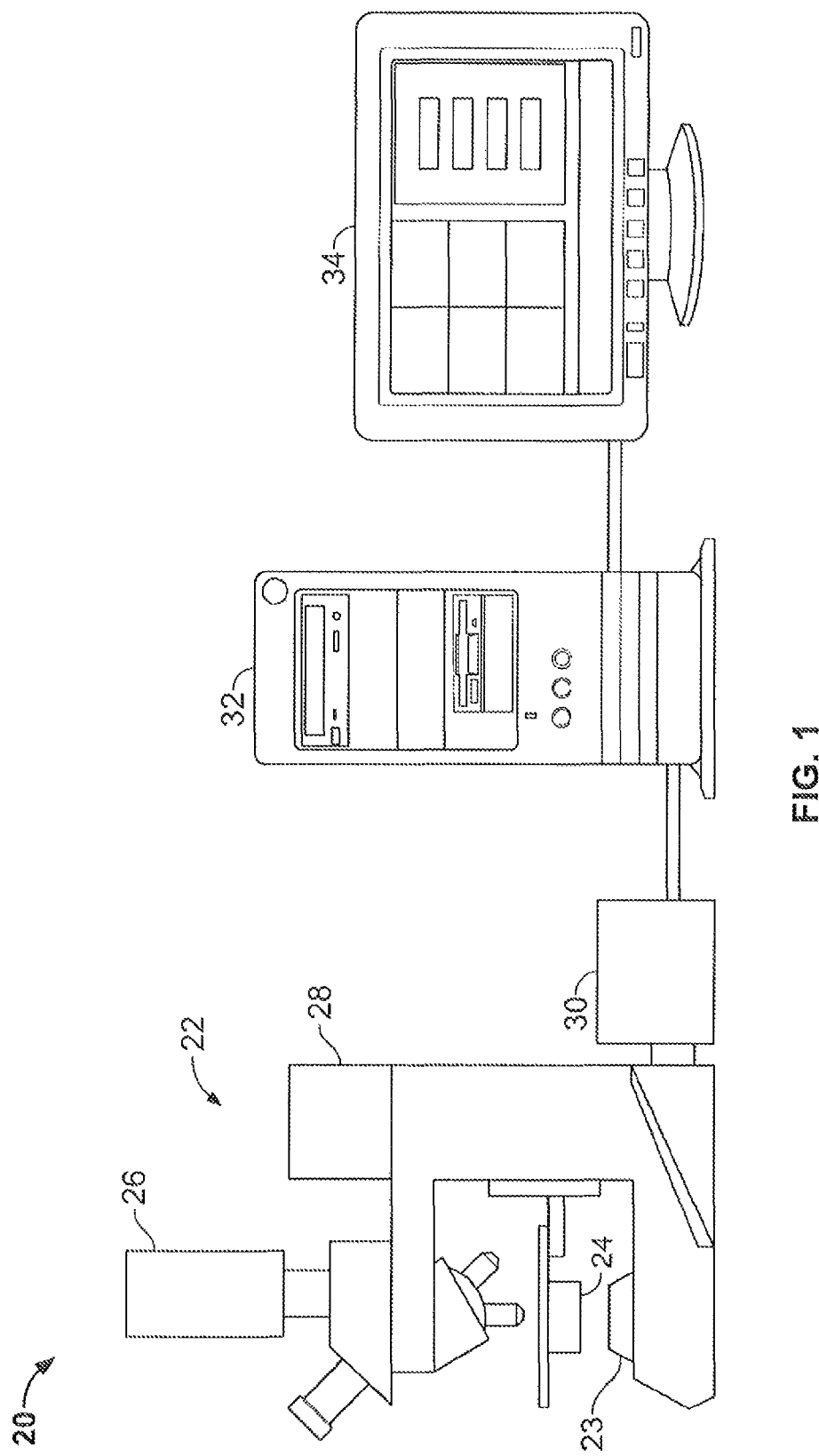
FIG. 1 is a diagrammatic view of the apparatus of the preferred embodiment of the invention.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

The methods of the various embodiments of the invention are preferably performed on a microscope system 20, as shown in FIG. 1. System 20 contains a microscope 22. In some embodiments microscope 22 is preferably an inverted type microscope. Microscope 22 comprises a source 23 of illumination, preferably visible-band illumination.

A motorized stage 24 and a camera 26 are mounted to microscope 22. In other embodiments a laser generator 28 is mounted adjacent thereto and coupled to a central controller 30. A computer 32, such as a PC or similar computer, and a monitor or display 34, is coupled to microscope system 20.

For practical use in pathology, in particular the diagnosis of cancer, it is imperative that the functionality, process workflows and the user-friendliness of the analysis method be tailored not only to the special requirements of this medical discipline but also to the special needs of the persons involved in this field. Furthermore, despite its numerous diagnostic advantages, the analysis method should remain economical, i.e. time- and money-saving. Amid these requirements, one is faced with the challenge of further refining the basic method described for practical use.

Figure 2:
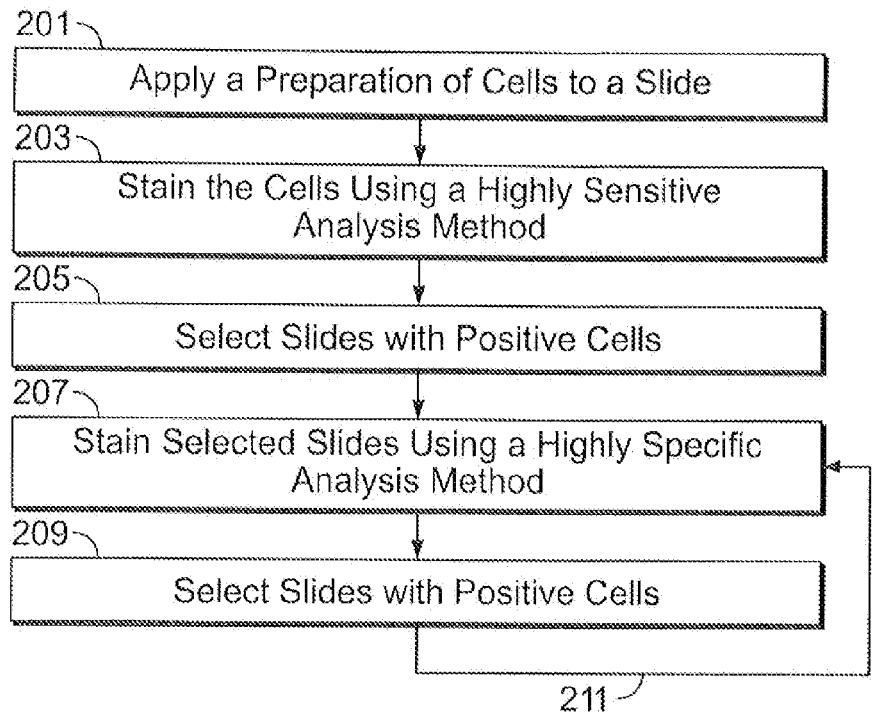
FIG. 2 is a chart of an embodiment of a method of the invention.

This challenge is solved according to a first aspect of the invention, where in a method of this type, a group of preparations with cells to be analyzed is stained using a stain of a highly sensitive analysis method and then only the preparations with positive findings are further processed, as shown in flow chart form in FIG. 2.

The use of this method for cell analysis is broken down into a series of steps, the number of which is determined by the analysis results gained in the individual steps (recursivity): Optimal economy of the entire analysis process is achieved if a strategy of a gradual narrowing of the analysis on uncertain findings is employed. A preparation of cells is applied to a slide (step 201). In a first process step, all preparations being studied are subjected to a highly sensitive analysis method (step 203). A high degree of sensitivity is achieved in general by lowering the threshold. This minimizes the risk of overlooking positive findings. However, it also inevitably increases the number of false positives (false alarms). The usefulness, however, can be found in the fact that this method eliminates negative findings from all further analyses. Preferably, cells with positive findings (both true and false positives) are selected (step 205). Only those cells are subjected to the further analytical step of staining with a stain for a highly specific analysis method (step 207). Cells with positive findings are then selected (step 209).

Subsequent analyses (step 211) are performed on any remaining preparations with uncertain findings using various analysis methods that, if necessary, require the preparations to be destained and restained again. As the procession of analyses progresses, the methods are selected so that the emphasis on high sensitivity at the cost of specificity is increasingly shifted in favor of specificity. The chain of analyses is only ended when all remaining uncertainties have been eliminated or the analysis options have been exhausted.

Figure 2A:
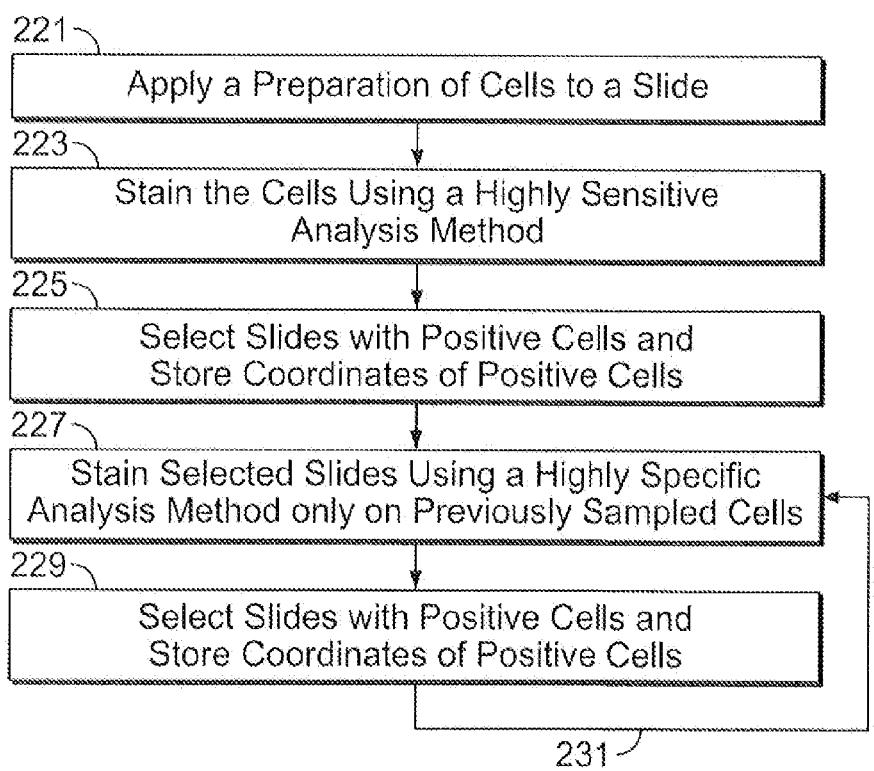
FIG. 2a is a chart of another embodiment of a method of the invention.

A further aspect of the invention that represents an inventive contribution for increasing efficiency and exists independently of the strategy of gradual narrowing described above is the gathering of a sample from the cells to be analyzed and the concentration of further analytical steps on this sample. The number of cells to be analyzed can be reduced by further analyzing only sampled cells. Furthermore, the sampling of cells can provide a control function for further analytical steps. As shown in FIG. 2a, this aspect of the invention has the steps of applying a preparation of cells to a slide (step 221), staining the cells using a highly sensitive analysis method (step 223), selecting slides with positive cells and storing the coordinates of the positive cells (step 225), staining selected slides using a highly specific analysis method only on previously sampled cells (step 227), and selecting slides with positive cells and storing the coordinates of those positive cells (step 229). Subsequent analyses (step 231) are performed on any remaining preparations with uncertain findings using various analysis methods that, if necessary, require the preparations to be destained and restained again. As the procession of analyses progresses, the methods are selected so that the emphasis on high sensitivity at the cost of specificity is increasingly shifted in favor of specificity. The chain of analyses is only ended when all remaining uncertainties have been eliminated or the analysis options have been exhausted.

Figure 3:
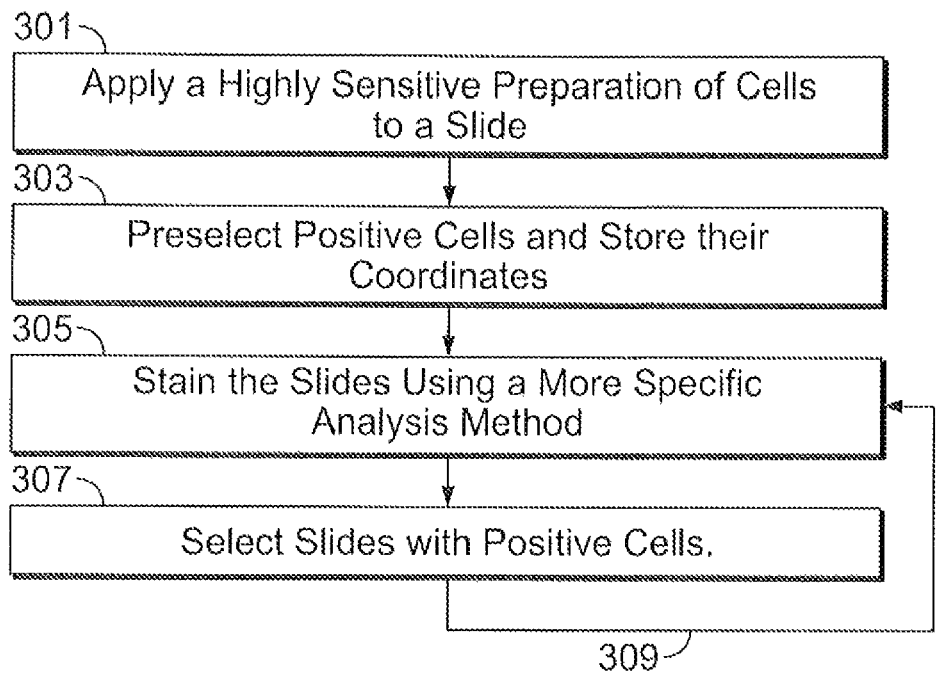
FIG. 3 is a chart of another embodiment of a method of the invention.

In a series of consecutive analytical steps, efficiency can be increased and the significance of the results can be heightened if a preselection is already made within the entire collection of the examined cells, as shown in FIG. 3. In this embodiment, a pre-analysis method is performed, including by way of example and not limitation the use of so-called immunocytochemical markers (e.g. $P16^{Ink4a}$ or L1-virus-capsid for the detection of uterine or cervical cancer), as will be hereinafter described in more detail.

As shown in FIG. 3, a highly sensitive preparation of cells is applied to a slide (step 301). Cells are preselected and their coordinates are stored (step 303). The slides are then stained using a more specific analysis method (step 305). Cells with positive findings are selected (step 307). Subsequent analyses (step 309) are performed on any remaining preparations with uncertain findings using various analysis methods that, if necessary, require the preparations to be destained and restained again.

The cell-related results of the respective preceding analytical step can be drawn upon, such as the classification according to cell type, the response to an immunocytochemical marker, a remarkable cell nucleus morphology detected through segmentation or a remarkable constellation of neighboring cells. If, according to this method, so-called "regions of interest" (ROIs) and/or even individual cells are identified and their coordinates added to the information accompanying the images to be stored, then further analyses can be concentrated on or even limited to the examination of identified cells. These cells can also provide a control function such as the division into analysis cells and reference cells necessary for certain analytical processes.

The cell sampling and, if necessary, classification can be performed manually under visual control: Images are taken at the desired microscope position with the operator using a joy stick or a foot button, for example. If necessary, individual cells are indexed with the aid of an interactive element such as joy stick or a mouse, rollerball or graphics tablet. All of these actions can be performed on computer display 34 receiving a constant feed from camera 26 or on which the taken or subsequently digitalized still image is displayed. An image generated by the connected computer 32 can be integrated into the optical path of the microscope 22, by means of which the position of an interactively positioned pointer or crosshairs can be superimposed on the optical microscope image.

Another aspect for increasing the efficiency of the application of the cell analysis method existing independently of the process steps listed above is the subjecting of a group of preparations with the cells to be analyzed to an automatic analytical step. For example, the first analytical step 303 of the method of FIG. 3 is, in this embodiment, automated. It is hereby advantageous if the automatic analytical step is used as a preanalysis to display suspicious cells. In an embodiment, the use of so-called immunocytochemical markers (e.g. $P16^{Ink4a}$ or L1-virus-capsid for the detection of uterine or cervical cancer) is significant in the starting phase of the analysis. Because the effect of these marker substances is the clear marking of cells at the slightest suspicion of a malignant transformation or the precursor thereof, the intended preselection can be performed with a high degree of automation. In particular, such marker demonstrations can be automatically searched with digital microscopes (these are devices in which the enlargement optics are optimized through the interaction with a digital camera and in which the eyepieces can be removed for direct viewing).

In particular, if the marker properties involve extensive staining of the cell nuclei and/or cytoplasm in the event of a positive reaction, which is the case with the marker substance $P16^{Ink4a}$, a linear scanner optimized to the dimensions of conventional microscope slides can be used. In this type of scanner, the two-dimensional sensor-array, the usual base element of digital camera 26, is replaced with a high-resolution linear sensor-array (line sensor), which is capable of scanning the desired preparation surface with a single linear movement orthogonal to the sensor axis.

Instead of a single-line sensor, a multi-line sensor or a combination of multiple single-line sensors arranged parallel to one another can be employed so that the lines of the light passing through the preparation are split through a prism for example and deflected via filters for different parts of the spectrum to the individual sensor lines so that a multi-channel, e.g. spectrally differentiated image is simultaneously recorded.

Although the optical resolutions possible with light microscopes cannot yet be achieved with the current state-of-the-art line sensors, the reduction to a continuous linear movement between optics and preparation instead of a two-dimensional step-movement considerably simplifies the mechanics and accelerates the scanning.

Existing independently from the described steps for increasing efficiency is an essential aspect aimed at improving the process technology. This is achieved through a further aspect of the invention, wherein the first digital image and the second digital image are aligned by having fine-tuning achieved through the merging of local image data.

If a selected preparation is subjected to a subsequent analysis, not only the regions established in the preceding analysis should be reexamined. Rather, the cells identified in the preceding examinations should also be reexamined and even be aligned with the precision of the optical resolution. At a desired precision of the alignment at the magnitude of a half wavelength of light this is mechanically impractical and extremely expensive.

Here the interaction of mechanical and digital adjustment mechanisms at a tolerable financial outlay leads to the desired success: It is already known that through a computer-controlled movement of the microscope table 24, the desired position can first be driven with the mechanical tolerance of the table positioning mechanism. The process then searches for correspondences in the constellation of cells or cell nuclei between the actual camera image and the images stored in the prior analytical step. From the linear, if necessary angular displacement between the images, a shift and, if necessary a rotation vector are calculated with which the table position is mechanically corrected.

Figure 4:
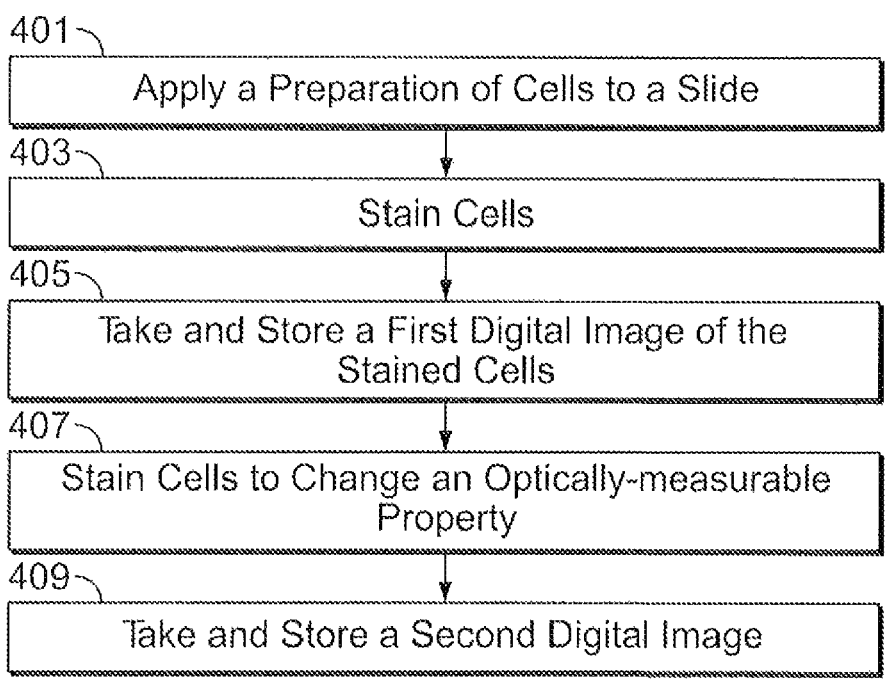
FIG. 4 is a chart of another embodiment of a method of the invention.
Figure 4A:
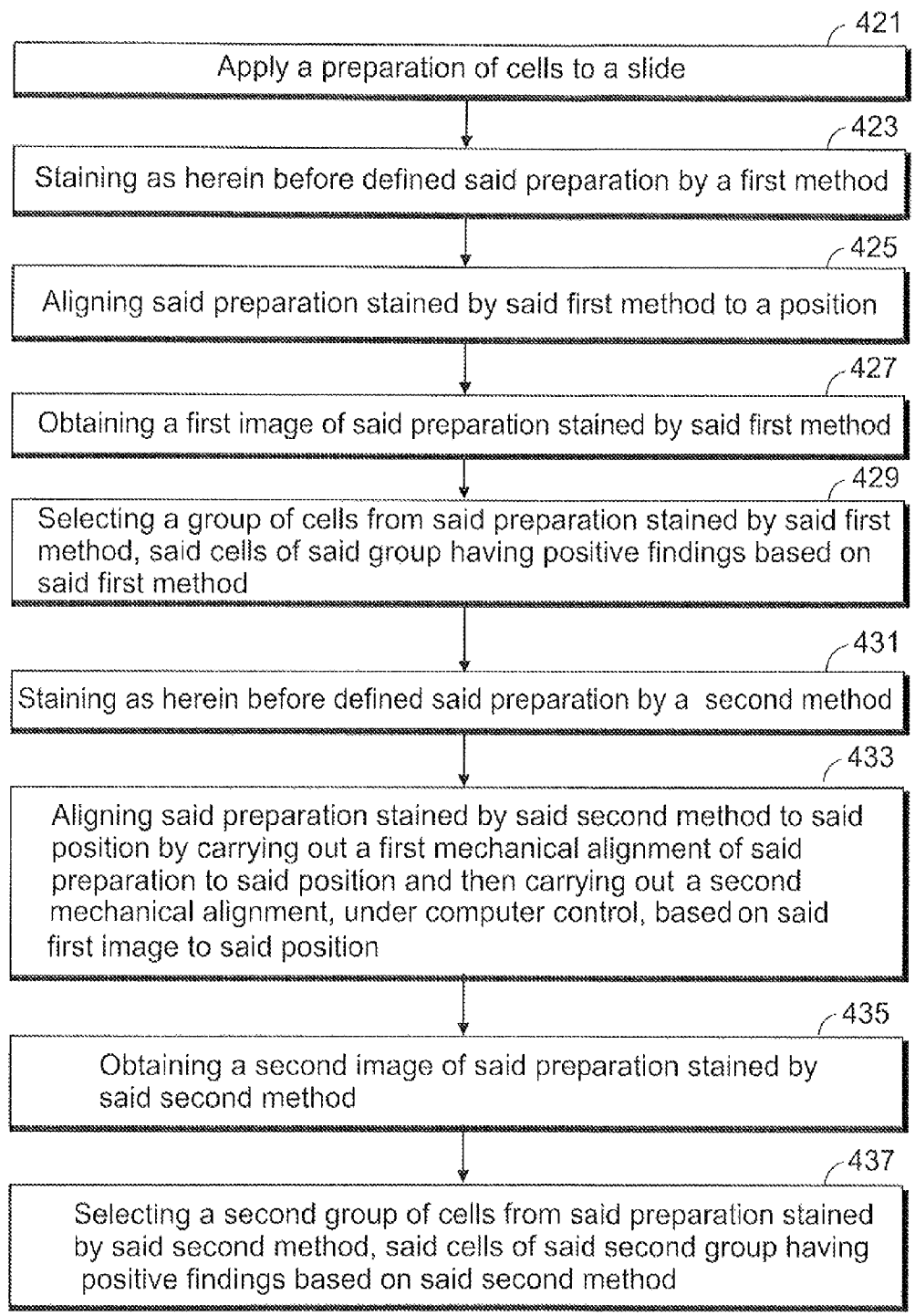
FIG. 4A is a chart of another embodiment of a method of the invention.

This method is illustrated in FIG. 4A, which shows the steps of applying a preparation of cells to a slide (421), staining as herein before defined said preparation by a first method (423), aligning said preparation stained by said first method to a position (425), obtaining a first image of said preparation stained by said first method (427), selecting a group of cells from said preparation stained by said first method, said cells of said group having positive findings based on said first method (429), staining as herein before defined said preparation by a second method (431), aligning said preparation stained by said second method to said position by carrying out a first mechanical alignment of said preparation to said position and then carrying out a second mechanical alignment, under computer control, based on said first image to said position (433), obtaining a second image of said preparation stained by said second method (435), selecting a second group of cells from said preparation stained by said second method, said cells of said second group having positive findings based on said second method (437).

A third step involves a digital fine-tuning using the known methods of digital image processing. [delete hard return] Fine-tuning of this type, which brings the evenness of coverage of the image of a cell in different stains to the precision of the optical resolution, is a necessary requirement if the merging of local image data is to be used for the improvement Of locally operating image analysis processes beyond the merging of cell-related analysis results. The segmentation processes such as the identification of the course of the cell nucleus membrane or the description of cytoplasm borders can profit from this.

For example, the cell nucleus membrane is easier to identify in a Feulgen-stain, while the cytoplasm membrane border is easier to identify in an MGG- or Papanicolaou stain. Furthermore, the analysis of cell regions determined by fine structuring on the basis of a multi-dimensional image vector of pixel values of the different stains can provide more illuminating additional information. It is thus advantageous if the cell regions determined by fine structuring are analyzed on the basis of a multi-dimensional image vector from the pixel values of different stains.

In a particular embodiment, the adjustment process can be hierarchically undertaken through consecutively taken sets of images by having the first digital image and the second digital image aligned by first having a larger area recorded at lower resolution and then having a smaller area recorded at higher resolution.

It is hereby advantageous if microscope slides with grids or marks, such as engraved lines, are used.

A special problem cells may present is that during the destaining- and restaining process some may become loosened from their original position and become deposited at a different position. These cells are referred to as "swimmers." A further aspect of the invention is therefore proposed, where cells that become loosened from their original position during a staining process are captured through seeking both absent as well as redundant objects and searching for a corresponding object. According to the invention, "swimmers" can thus be captured by searching for the absent as well as redundant objects when examining the correspondence of the cell or cell nuclei constellations mentioned above. If a corresponding object can be found on the basis of morphological features, for example, the diagnostically relevant features can also be merged for these cells.

Another aspect of the invention provides for a histological study in which the tissue area to be analyzed is established. The invention thus concerns joining the method to histology for the purpose of yielding more precise histological findings. A cytological subsequent examination thus follows a histological study.

In this case, the sequence generally proceeds as follows: A tissue sample is fixed in formalin and then embedded in paraffin. From this tissue block, a thin section is taken in which cells are evaluated under the microscope following HE-staining, for example. Normally, ROIs (regions of interest) are "traced" with a pencil on the cover plate. These in general very rough demarcations of the ROIs are applied to the surface of the tissue and incised with a scalpel. A section measuring approximately 50 to 70 µm thick is then removed, from which the ROIs can be detached as a result of the etching of the ROI-demarcations performed beforehand. The cells from this section are enzymatically isolated, the cell nuclei isolated, placed on a microscope slide glass for cytological examination and subjected to cell nuclei analysis following Feulgen-staining for example.

In a method of this type, it is advantageous if the cells are classified. The results of a subsequent cell nuclei analysis are especially illuminating if the collection of the cells gathered in this way can be classified as suspicious specimens, in particular those from subareas of the tissue section that can be more narrowly demarcated, as well as both normal cells and reference cells.

Because the location information is lost in the cell isolation process, material-specific cell nuclei characteristics are also inventively used in a classification if necessary. This can be morphological particularities for which the criteria is established by means of an analysis of significant nucleus shape characteristics (nucleus surface, ovality, nucleoli sizes, etc.) of cells interactively sampled in the histological preparation, so that cell nuclei of comparable form can be automatically arranged in the cytological preparation.

It is advantageous if the cells to be analyzed can be removed from the histological preparation with a computer-controlled scalpel. The retracing of the demarcations marked with a scalpel under the microscope required for the removal of the ROIs mentioned above can also be computer-supported by having the demarcations interactively input and having the scalpel controlled by computer. In this way, the ROIs can be demarcated more precisely allowing the portion of the cell nuclei in the diagnostically relevant areas to be relatively increased in the resulting material.

A last step of an analysis method can be the release—mechanical if necessary—of individual cells for the purpose of molecular biological analysis (e.g. a DNA-analysis by means of polymerase-chain-reaction). This is conventionally performed by having the desired cells separated from the microscope slide with a microdissection needle under visual, microscopic control after the cover glass is removed and then suctioning the cells with a capillary tube placed directly over them.

According to a further aspect of the invention, this process is supported by a cell analysis device that allows the cell to be driven automatically and computer-supported. The desired position known from the preceding examinations is hereby used.

Another aspect of the invention, which is also inventive independently of the measures described above, provides that a material is adhesively applied to the cells on the slide, the adhesion properties of which are increased with a laser beam, and that the coordinates of previously selected cells can be controlled with a positionally-controllable laser.

The time and expenses for a molecular biological analysis of one or a few cells is generally justifiable only for research. The time and expenses can be reduced if larger collections of cells can be made available. According to the invention, this is achieved with the following measures: If the cells to be placed together are identified and their coordinates are marked, the cover glass is removed. A material such as a film, for example, the surface of which becomes adhesive when subjected to moderate heating, is then applied to the preparation. This adhesiveness can be achieved by coating the film with a material used in known hot-melt adhesives. The effect can also be found in the film itself if, for example, it is made of a material that develops adhesive properties in the melting phase.

Through a punctual heating by means of a position-controlled laser at the coordinates of the previously selected cells, this effect can be used to affix the cells to the film. Following this step, the film is then lifted off and the cells lifted off with it are removed and collected for further analysis. The film can be pigmented for maximum absorption of the laser beam energy and continued protection of the cells. Positional control of the laser beam can be realized by integrating the beam guidance in the analysis microscope.

A further aspect of the invention is increasing the usability and acceptance of the new methods through improved functional design of the technical concept. It should be taken into consideration that pathologists require highly versatile instruments for their work. The use of a database-based workstation system is thus proposed independently from the previously described aspects of the invention.

Technically spoken, the application of the methods described in the invention with the utilization of all described options and modifications opens a multidimensional feature space that the pathologist should be able to assemble on a case-related basis. This requires digital workstation systems that are outfitted according to use and, if necessary, are supported by a practical digital infrastructure.

Such workstation systems can be closed devices that comprise a workstation computer and a digitally controllable microscope equipped with a digital camera. They can also be components of a network of shared workstation systems. These can be specialized for subtasks of the entire analysis process such as preselection, analysis with or without visually interactive control or evaluation of the analysis results and generating the findings on the basis of the consolidated analysis results and accompanying information. The workflow can be supported by networked central systems for organization, workflow control, image and data archiving, accounting, as well as communication with external systems (central hospital information systems, PACS, telemedicine-networks) and, if necessary, controlled in the sense of a workflow-architecture.

The architecture of the workstation system is database-based, where the database can be realized as a local or central network server. Among other functions, the database facilitates the recording of all images taken and their accompanying information. This primarily includes the identification data of the preparations, coordinates of all actions performed on the preparation and in the images, as well as all analysis data such as contours, measurement values and classification, for example.

The analysis functions are preferably designed as modular. They access a common repository of basic functions, such as imaging operations, graphic representation objects, interaction elements and I/O functions. The software platform can be understood as a specialized operating system that is based on a standard operating system. This architecture allows for one the uniform and continuous operation of various function modules and the displaying of their various analysis results.

The workstation system offers the possibilities of setting function sequences based on the case-specific clinical objective and formatting the results display in a practical manner. This can be based on the material used (for example, cervical smear, fine needle aspiration of the prostate or pancreas, urine or bronchial secretion), on the type of analysis method to be used (for example, DNA-image cytometry, immunocytochemistry, fluorescence-in-situ-hybridization (FISH), AgNOR-analysis, chromatin pattern analysis), on the staining processes employed (for example, MGG, Papanicolaou, pararosaniline, thionine, AEC, Texas red, fluorescein), on the markers used (for example, p16, Ki67, BerEP4, L1-capside, chromosome-1), on the cell compartments to be analyzed (for example, cell nucleus, nucleoli, cytoplasm), on the diagnostic clinical objective (for example, type of tumor, benign/malignant, degree of malignancy, location of the primary tumor when metastasis is involved), on the microscopy procedure (for example, transmitted light, dark-light, fluorescence), on diagnostic "algorithm" (for example, percentage of positive cells, size and/or number of AgNORs, DNA-stem line ploidy and 9c-exceeding rate, number of cells without chromosome 1) and finally on feasible or desired degree of automation (for example, visual-interactive, computer-supported, semiautomatic, fully automatic).

The results can be presented in the form of numerical values, tables, histograms or class groupings. Controlling the process flow can be simplified through the use of a symbolic representation of all actions on a so-called "virtual slide" (a digital representation of the microscope slide).

The invention describes a collection of measures optimizing the process of cell analysis, as shown in FIG. 4, in which cells are adhesively applied to a slide (step 401), the cells are stained with a stain (step 403), a first digital image is taken of the stained cells applied to the slide and the first digital image is stored (step 405), the same cells on the same slide are treated with a second stain (step 407), after the first digital image is taken, that changes an optically-measurable property of the cells, and a second digital image of the cells applied to the slide is taken and stored (step 409). The individual measures are inventive independently of one another. For the person skilled in the art, a plethora of innovations with easily understood practical implementation can be derived from the description. Therefore, this document foregoes presenting a plurality of embodiments for the individual aspects of the invention.

Figure 5:
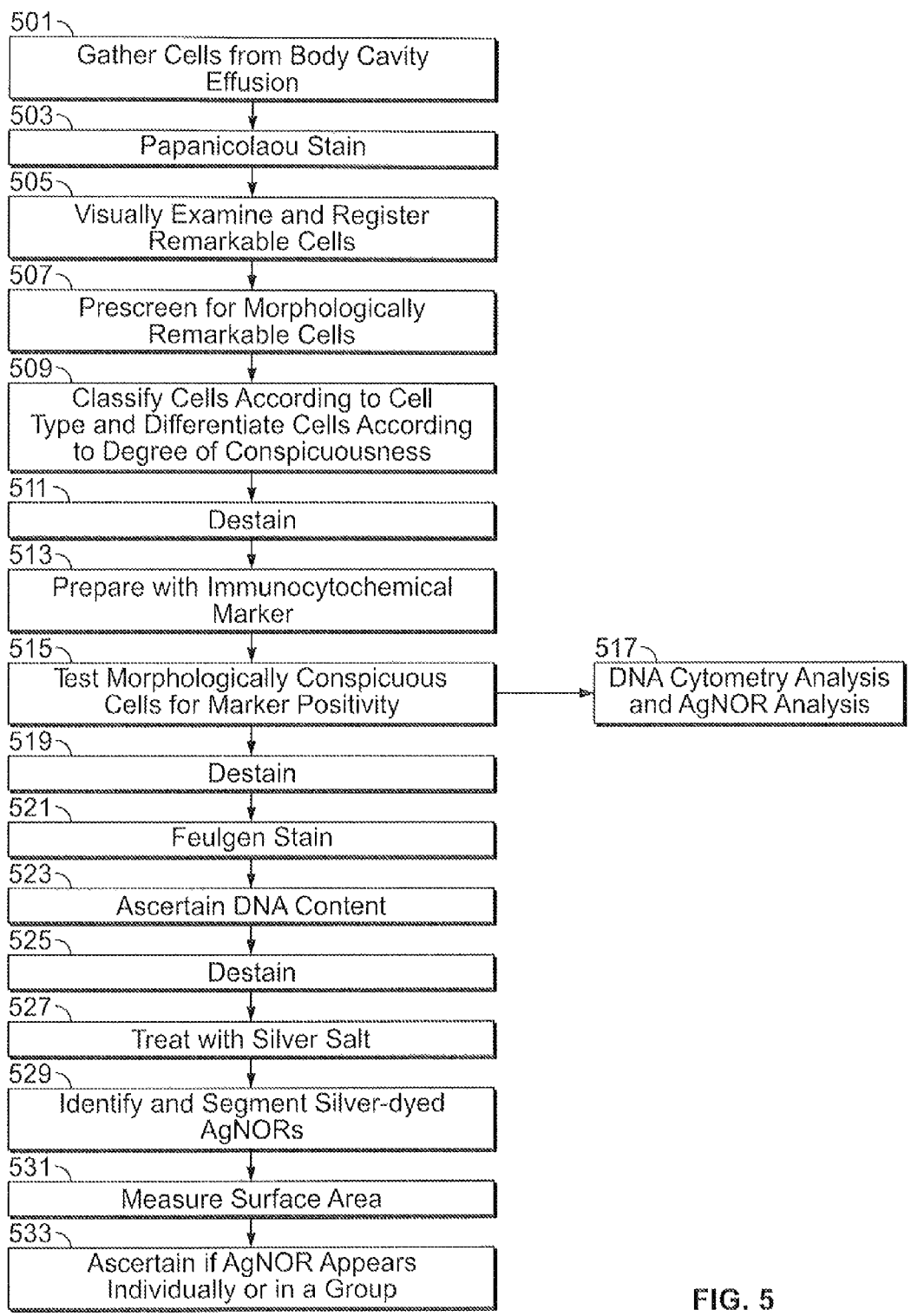
FIG. 5 is a chart of another embodiment of a method of the invention.

The basic premise of the invention, however, will be illustrated through a preferred embodiment, diagrammed in FIG. 5, that serves to diagnose a malignant mesothelioma or a metastasizing cancer using a small collection of cells from a body cavity effusion.

An example of a medical task in which the inventive device can be advantageously employed is the early diagnosis of pleural cancer (malignant mesothelioma) as well as in differentiating this disease from a metastasizing cancer in cell material that can be gathered from body cavity effusion. To achieve an especially high degree of diagnostic accuracy, up to four consecutive analytical steps can be employed that are each based on the treatment of microscopic cell preparations with different stains or marker demonstrations. First, a preparation of cells is gathered from a body cavity effusion (step 501). As little as 100 cells in which an appropriate constellation of analysis results has been found through the analysis chain described below is sufficient for issuing one of the diagnoses named above, as a medical study has confirmed (Pomjanski N et al., *Early Diagnosis of Mesothelioma in Serous Effusions Using AgNOR Analysis*; ANALYTICAL AND QUANTITATIVE CYTOLOGY AND HISTOLOGY, 23 Nr. 2 (2001) pp 152-159) (the disclosure of which is incorporated herein by reference).

The analysis of cell material starts with Papanicolaou staining, which stains both the cell nuclei and the cytoplasm (step 503). This staining is especially well suited for the visual evaluation of cell morphology. In this analytical step, the microscopic preparation is visually examined. Remarkable cells are registered, i.e. if one or more such cells are present in a field of vision, an interaction element, such as joy stick 4 or a foot button, is activated, by means of which a coordinate-measuring procedure and, if necessary, digital imaging are triggered (step 505). The use of automatable morphometric processes for prescreening morphologically remarkable cells can also be considered as a possibility (step 507). This process is a collection of digital image analysis processes in which dimensions are derived according to cell nucleus and/or cytoplasm segmentation from the contour tracing, where the dimension can be used to characterize the form and structural characteristics. An automatic classification device can be called upon to classify cells according to cell type and to differentiate them according to their degree of conspicuousness based on morphometric characteristics (509). Preparations without any conspicuous features are eliminated following this step.

After the cover glass is lifted, the preparation is destained (step 511) and then prepared with an immunocytochemical marker—calretinin or BerEP4 (step 513). Calretinin only stains mesotheliomal cells, while BerEP4 only stains cells of epithelia origin, thus most cancer cells. The cells previously labeled as morphologically conspicuous can now be tested for their marker positivity (step 515). If necessary, the entire preparation can be searched for marker-positive cells. This procedure can be performed automatically, because marker-positive cells are easily distinguished from marker-negative cells. The cells marked and identified in this way can be individually directed into the subsequent analytical steps. In the case of marker-positivity of morphologically suspicious cells, a subsequent DNA-cytometry (evidence of polyploidization, $3^{rd}$ analytical step) as well as an AgNOR-analysis (criteria: more than 4.5 AgNORs per cell nucleus in medium, $4^{th}$ analytical step) are performed (step 517). The subsequent analytical steps serve for confirming the provisional diagnosis of "malignant mesothelioma" in the event of calretinin positivity (Pomjanski et al, 2001), while in the event of BerEP4-positivity of cells in the effusion sediment they serve for confirming the provisional diagnosis of metastasizing cancer cells (Motherby et al, 1999).

After being destained once again (step 519), the preparation is prepared with a Feulgen stain (step 521) that stoichiometrically reacts with the DNA of the cell nucleus. This serves the purpose of ascertaining the DNA-content (step 523), which represents an indicator for an elapsed or developing transformation of the cell to a tumor cell. Cells that require further clarification following the results of the analyses already performed are automatically directed under the microscope, their cell nuclei are segmented and an integral measurement of the optical density is performed within the located contour. Following various known calibration and correction procedures, the DNA-content of the cell is derived from this measurement.

It can be necessary to further differentiate and type suspected tumor cells identified in the previous analyses. This is where the analysis of the AgNORs can play a role. AgNORs are nucleus proteins, the number, size and arrangement of which may provide information on the presence or aggressiveness of a tumor. After being destained once again (step 525), the preparation is treated with a silver salt solution (step 527). The silver binding AgNORs are dyed brown. Within the cell nuclei of the cells being examined, only a segmentation of the silver-dyed AgNORs is performed. The evaluation of the cell contour gathered in the previous analytical step serves in a supporting function, since this cell contour is only faintly visible in the present staining. A segmentation of the nucleoli within the cell contour that can advantageously be performed in the Feulgen staining is helpful because the detection of nucleoli contours provides relevant additional information for the differentiation of the AgNORs. Following the identification and segmentation of the AgNORs (step 529), surface area is measured (step 531). It is then ascertained whether an AgNOR appears individually ("satellite") or in a group ("cluster") (step 533). This analytical step is also performed automatically.

The diagnostic significance of the results of the elapsed analytical chain is purposefully illustrated in the table shown in FIG. 6.

A clear diagnosis of mesothelioma or cancer cannot be issued based on the results of an analytical step taken on its own. As in other applications with a selection and combination of analytical methods adapted to the diagnostic clinical objective, this establishes the diagnostic progress that can be achieved through the use of a method and device according to the invention.

While preferred embodiments of the present invention are shown and described, it is envisioned that those skilled in the art may devise various modifications of the present invention without departing from the spirit and scope of the appended claims.

We claim:

1. A method of cell analysis comprising:
   applying a preparation of cells to a slide;
   staining said preparation of cells by a first method;
   aligning said preparation of cells stained by said first method to a position;
   obtaining a first image of said preparation of cells stained by said first method;
   selecting a group of cells from said preparation of cells stained by said first method, said cells of said group having positive findings based on said first method;
   staining said preparation of cells by a second method;
   mechanically aligning said preparation of cells stained by said second method to said position and then digitally aligning, under computer control, said preparation of cells stained by said second method to said position based on said first image;
   obtaining an image of said preparation of cells stained by said second method;
   selecting a second group of cells from said preparation of cells stained by said second method, said cells of said second group having positive findings based on said second method.

2. The method of claim 1, wherein said first method is highly specific.

3. The method of claim 1, wherein said second method is highly sensitive.

4. The method of claim 3, wherein said first method is highly specific.

5. The method of claim 1, further comprising an automatic analysis step.

6. The method of claim 5, wherein said automatic analysis step comprises a pre-analysis step.

7. The method of claim 1, further comprising taking a digital image of said cells after said first staining step.

8. The method of claim 7, wherein said digital image is generated by a linear scanner.

9. The method of claim 1, further comprising taking a digital image of said cells after said second step.

10. The method of claim 9, wherein said digital image is generated by a linear scanner.

11. The method of claim 1, further comprising:
    taking a first digital image of said cells after said first staining step;
    taking a second digital image of said cells after said second staining step; and
    aligning said first digital image and said second digital image by fine-tuning through the merging of local image data.

12. The method of claim 11, further comprising ascertaining cell areas through fine structuring.

13. The method of claim 12, further comprising analyzing said cell areas on the basis of a multidimensional image vector, said vector generated from pixel values of said first digital image and said second digital image.

14. The method of claim 13, wherein said aligning step comprises capturing a first area at a first resolution and capturing a second area at a second resolution, said first area being larger than said second area and said first resolution being lower than said second resolution.

15. The method of claim 1, wherein said slide has at least one of grids and markers.

16. The method of claim 1, further comprising capturing cells detached during said first staining step or said second staining step by searching for an absent object and a redundant object and searching for a corresponding pair of objects.

17. The method of claim 1, further comprising a histological study of a tissue area of said preparation of cells.

18. The method of claim 17, further comprising classifying said cells.

19. The method of claim 18, wherein said classifying step uses a property of a nucleus of said cells.

20. The method of claim 17, further comprising harvesting said cells with a computer-supported scalpel.

21. The method of claim 20, wherein said scalpel is automatically driven by a computer.

22. The method of claim 21, wherein said preparation of cells are adhesively applied to said slide, the method further comprising:
    applying a material to said preparation of cells;
    increasing an adhesive property of said material with a laser beam;
    irradiating previously-sampled cells with a positionally-controllable laser.

23. The method of claim 1, further comprising using a database-based workstation system.

* * * * *